United States Patent
Yamada et al.

(10) Patent No.: US 7,868,771 B2
(45) Date of Patent: Jan. 11, 2011

(54) DOZE-OFF WARNING APPARATUS FOR VEHICLE

(75) Inventors: Kiichi Yamada, Chiba (JP); Minakami Yumi, Chiba (JP)

(73) Assignees: Hyundai Motor Company, Seoul (KR); Kia Motors Corporation, Seoul (KR); Hyudai Motor Japan R&D Center, Inc., Chiba (JP)

( * ) Notice: Subject to any disclaimer, the term of this patent is extended or adjusted under 35 U.S.C. 154(b) by 254 days.

(21) Appl. No.: 12/276,875

(22) Filed: Nov. 24, 2008

(65) Prior Publication Data

US 2009/0237257 A1   Sep. 24, 2009

(30) Foreign Application Priority Data

Mar. 18, 2008   (JP)   .............................. 2008-069195

(51) Int. Cl.
*G08B 23/00* (2006.01)
(52) U.S. Cl. .................... 340/575; 340/573.1; 351/200; 180/271
(58) Field of Classification Search ................. 340/575, 340/576, 573.1, 573.2, 937; 351/200; 180/271, 180/272
See application file for complete search history.

(56) References Cited

U.S. PATENT DOCUMENTS

| | | | | |
|---|---|---|---|---|
| 5,573,006 A | * | 11/1996 | Shimotani et al. | 600/558 |
| 5,786,765 A | * | 7/1998 | Kumakura et al. | 340/576 |
| 6,717,518 B1 | * | 4/2004 | Pirim et al. | 340/576 |
| 7,071,831 B2 | * | 7/2006 | Johns | 340/576 |
| 7,202,792 B2 | * | 4/2007 | Zhang et al. | 340/575 |

FOREIGN PATENT DOCUMENTS

| | | |
|---|---|---|
| JP | 08-153288 | 6/1996 |
| JP | 10-315799 | 12/1998 |
| JP | 11-339200 A | 12/1999 |
| JP | 2000-035313 | 2/2000 |
| JP | 2000-301962 | 10/2000 |
| JP | 2001-010368 | 1/2001 |

\* cited by examiner

*Primary Examiner*—George A Bugg
*Assistant Examiner*—Edny Labbees
(74) *Attorney, Agent, or Firm*—Edwards Angell Palmer & Dodge LLP; Peter F. Corless

(57) ABSTRACT

The present invention provides a doze-off warning apparatus for a vehicle, comprising: a sensor measuring a driver's eye-open time ($t_o$) and an eye-closure time ($t_c$); a doze-off driving determination part determining degree of danger based on the measured eye-open time ($t_o$) and the eye-closure time ($t_c$) and comparing the determined degree of danger with a predetermined threshold (Kt); and an alarm part providing a warning signal with the driver when the degree of danger exceeds the predetermined threshold (Kt).

5 Claims, 2 Drawing Sheets

DOZE-OFF WARNING APPARATUS FOR VEHICLE

CROSS-REFERENCE TO RELATED APPLICATION

This application claims under 35 U.S.C. §119(a) the benefit of Japanese Patent Application No. 2008-0069195 filed on Mar. 18, 2008, the entire contents of which are incorporated herein by reference.

BACKGROUND (a) Technical Field

The present Invention relates to an apparatus for warning a vehicle driver of danger of doze-off driving, in which driver's distraction caused by drowsiness is determined based on time of closure/open of driver's eye.

(b) Technical Background

Recently, the death toll by traffic accidents increases in substantially proportion to increase of vehicles. In order to decrease the death toll by traffic accidents, various efforts are made to develop advanced safety vehicle (ASV) all over the world. The ASV is designed to provide a driver with comfort, to decrease death toll by traffic accidents, and to be easy to drive as well. A basic concept of the ASV is to prevent accidents in advance such that safety of pedestrians and the vehicle itself can be ensured. Examples of technologies employed in the ASV include a doze-off state detection system, a night obstacle detection system, and a warning system of distance between cars.

Japanese Patent Application Publication No. H11-339200 teaches a doze-off state detection system in which frequency of eyeblink of the driver, speed of eyeblink of the driver, open degree of the eye, and time of closure of the eye are used as criteria to determine drowsiness.

Moreover, Japanese Patent Application Publication No. H09-277849 teaches another system in which time of eyeblink of a driver is detected and frequency distribution of the detected eyeblink time is used to determine the degree of decrease of the driver's attention.

Moreover, Japanese Patent No. 3509839 discloses an apparatus for estimating the degree of driver's attention based on a value of drowsiness calculated on the basis of horizontal movement of driver's eyeball and a ratio of the number of long time eyeblink to the total number of eyeblink for a predetermined time period.

There is, however, an individual deviation in the correlation between the time and frequency of eyeblink and the degree of doze-off.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

An object of the present invention is to provide a doze-off warning apparatus in which danger of doze-off driving is determined by detecting duration of closure time of driver's eye rather than degree of doze itself.

In one aspect, the present invention provides a doze-off warning apparatus for a vehicle. The apparatus may comprise: a sensor measuring a driver's eye-open time ($t_o$) and an eye-closure time ($t_c$); a doze-off driving determination part determining degree of danger based on the measured eye-open time ($t_o$) and the eye-closure time ($t_c$) and comparing the determined degree of danger with a predetermined threshold (Kt); and an alarm part providing a warning signal with the driver when the degree of danger exceeds the predetermined threshold (Kt).

Preferably, the sensor may comprise a camera for capturing an image of the driver's eyes. From the captured image date, the eye-open time ($t_o$) and the eye-closure time ($t_c$) are obtained and then output to the doze-off driving determination part.

Suitably, the degree of danger may be obtained by dividing $Tc^n$ by To, wherein the 'n' is an integer.

Suitably, the threshold (Kt) can be empirically obtained from relationship between the degree of danger ($Tc^n$/To) and dangerous driving states.

Preferably, the doze-off driving determination part may perform the steps comprising: receiving the eye-open time ($t_o$) and the eye-closure time ($t_c$) from the sensor; exponentiating the eye-closure time ($t_c$); moving averaging the exponentiation of the eye-closure time ($t_c$) and the eye-open time ($t_o$), respectively, in time-series manner; calculating the degree of danger; and comparing the calculated degree of danger with the predetermined threshold (Kt).

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein.

Figure 1:
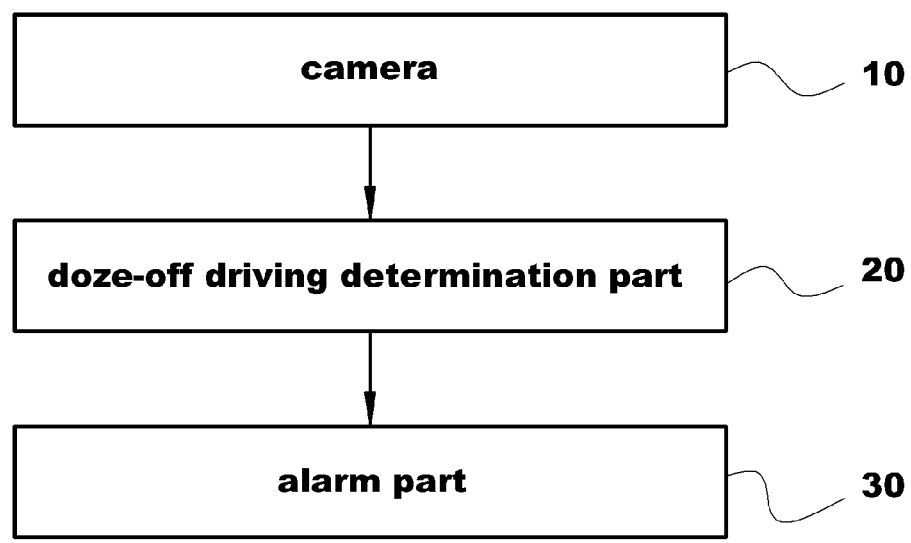
FIG. 1 is a schematic diagram of a doze-off warning apparatus according to a preferred embodiment of the present invention.

Reference numerals set forth in the drawings includes reference to the following elements as further discussed below:
10: camera 20: doze-off driving determination part
30: alarm part
101: receipt of eye-open time and the eye-closure time
102: exponentiation of the eye-closure time
103: average
104: calculation of degree of danger
105: comparison of degree of danger with threshold (Kt)
106: warning It should be understood that the appended drawings are not necessarily to scale, presenting a somewhat simplified representation of various preferred features illustrative of the basic principles of the invention. The specific design features of the present invention as disclosed herein, including, for example, specific dimensions, orientation, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, example of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiment, but also various alternatives, modifications, equivalents and other embodiments, which may be included within the spirit and scope of the invention as defined by the appended claims.

A doze-off warning apparatus is configured to determine that dangerous condition occurs when the duration of eye closure (hereinafter "eye-closure time") exceeds a certain threshold value. There is no individual deviation in the relationship between eye-closure time and degree of danger during driving.

Depending on the speed of a vehicle, the eye-closure time exceeding one second may be considered as being dangerous condition. Taking this into account, according to the present invention, the eye-closure time is subjected to exponentiation.

Moreover, considering the eye-open time would relatively decrease as the eye-closure time increases, according to the present invention, the eye-closure time is divided by the eye-open time to enhance the detection sensitivity of the degree of danger.

Further, the present invention employs a time series moving average to eliminate the deviation that can occur in each detection of the driver's eye, thereby improving the accuracy of determination of the danger of doze-off driving.

Referring to FIG. 1, a doze-off warning apparatus according to an embodiment of the present invention comprises a camera (10) for detecting an eye-closure time ($t_c$) and an eye-open time ($t_o$) per one eyeblink. The detected eye-closure time ($t_c$) is raised to the power of 'n' to obtain exponentiation of the eye-closure time ($t_c^n$).

The apparatus further comprises a doze-off driving determination part (20) that serves to calculate degree of danger ($Tc^n/To$) based on time-series moving averages of the eye-open time ($t_o$) and exponentiation of the eye-closure time ($t_c^n$) and to compare the calculated degree of danger with a predetermined threshold (Kt).

The apparatus is furnished with an alarm part (30) which is configured to receive data regarding the comparison result from the doze-off driving determination part (20) and to give a warning signal to the driver in case where the degree of danger ($Tc^n/To$) exceeds the predetermined threshold (Kt).

The threshold (Kt) can be derived from a relationship between the degree of danger ($Tc^n/To$) and dangerous driving states such as a rear-end collision, deviation from a lane and so forth. The relationship can be empirically defined by repeated experiments depending on specific driving conditions.

Since the dangerous driving states are mainly caused by failure of concentration on a front view, the dangerous driving states basically depends on eye closure time. The threshold (Kt) corresponds to degree of danger in driving. One or more threshold values can be set depending on specific driving conditions. The exponent 'n', which is used for exponentiation of eye-closure time, is set to 1 or more (generally, at least 2). For example, in case that 'n' is set to 2 and the eye-closure time is 2 seconds, the degree of danger can be adjusted to be four times the degree of danger when the eye-closure time is 1 second. On the other hand, the time-series moving averages may be calculated based on the past 50 times of eyeblinks (e.g., for approximately one minute).

Figure 2:
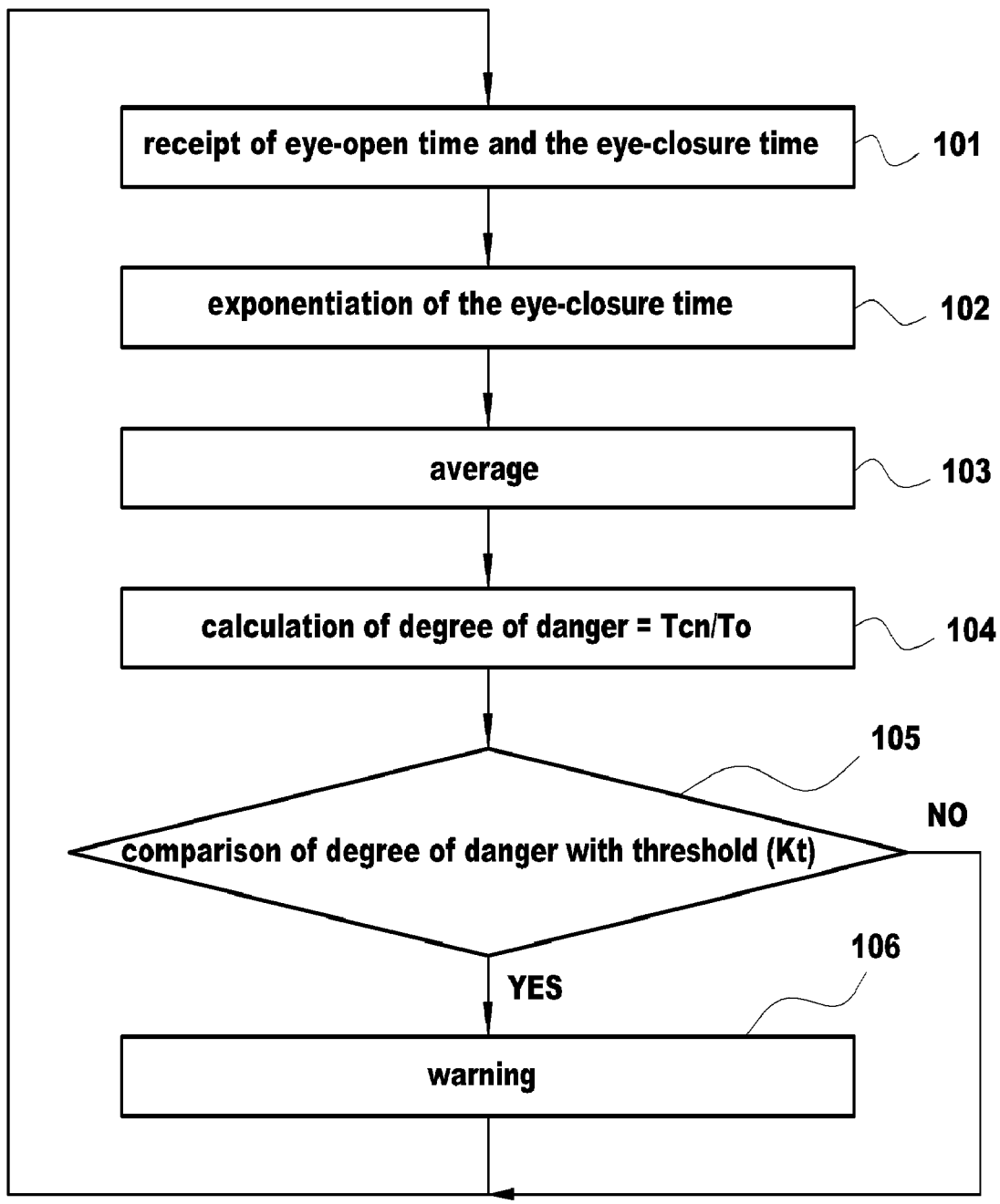
FIG. 2 is a flow chart illustrating a method of warning of doze-off driving according to a preferred embodiment of the present invention.

With reference to FIG. 2, a method of warning of doze-off driving with the above-described apparatus will be detailed hereinafter.

First, the camera (10) captures an image of a driver's face and transmits the image in the form of an image signal with grey level to the doze-off driving determination part (20). The doze-off driving determination part (20) detects a state of the driver's eye by means of binary-process of the grey leveled image. In particular, the binary-process of the image defines a degree of eye open by identifying states of eyelids, and generates an eye-closure time (time duration that a driver closes his/her eyes) and an eye-open time (time duration that a driver opens his/her eyes).

Further, the doze-off driving determination part (20) reads out the eye-closure time and the eye-open time per one eyeblink from the captured image. The read-out data is fed into a control unit (40) of the doze-off driving determination part (S101). The control unit (40) raises the received eye-closure time (second) to the power of 'n' (S102) and produce a time series moving average of the received eye-open time and the exponentiated eye-closure time (S103), and thereafter calculate the degree of the danger based on the foregoing parameters as shown in the following equation (S104).

'Degree of danger=Average of exponentiation of the eye-closure time ($Tc^n$)/Average of the eye-open time ($To$)'

Upon calculation of the degree of danger, the doze-off driving determination part (20) compares the degree of danger with a predetermined threshold (Kt), which may be suitably stored in a memory (S105), and outputs data regarding the comparison result to the alarm part (30) in case where the degree of danger ($Tc^n/To$) exceeds the predetermined threshold (Kt).

The alarm part (30), after receiving the data, generates a warning signal such as voice (for example, "take a break" or "drive carefully") or sound (for example, beep sound), thereby refreshing the driver's attention and thus ensuring safe driving.

According to the present invention, the apparatus is advantageously more sensitive to detect the driver's state since the eye-closure time is emphasized by exponentiation and such exponentiation of the eye-closure time is further emphasized by dividing the same by the eye-open time. Furthermore, since the threshold for determining the danger of doze-off driving is not based on learning-based data in connection with the driver, there is no significant difference between each individual in the threshold, whereby improving reliability on determination of the danger of doze-off driving.

The invention has been described in detail with reference to the preferred embodiment thereof. However, it will be appreciated by those skilled in the art that changes may be made in these embodiments without departing from the principles and spirits of the invention, the scope of which is defined in the appended claims and their equivalents.

What is claimed is:

1. A doze-off warning apparatus for a vehicle, comprising:
a sensor measuring a driver's eye-open time ($t_o$) and an eye-closure time ($t_c$);
a doze-off driving determination part determining degree of danger based on the measured eye-open time ($t_o$) and the eye-closure time ($t_c$) and comparing the determined degree of danger with a predetermined threshold (Kt); and
an alarm part providing a warning signal with the driver when the degree of danger exceeds the predetermined threshold (Kt),
wherein the degree of danger is calculated by dividing $Tc^n$ by To, wherein the 'n' is an integer.

2. The apparatus according to claim 1, wherein the sensor comprises a camera for capturing an image of the driver's eyes, from which the eye-open time ($t_o$) and the eye-closure time ($t_c$) are obtained and output to the doze-off driving determination part.

3. The apparatus according to claim 1, wherein the threshold (Kt) is obtained from relationship between the degree of danger ($Tc^n/To$) and dangerous driving states, which is set based on empirical data.

4. The apparatus according to claim 1, wherein the doze-off driving determination part performs the steps comprising:
receiving the eye-open time ($t_o$) and the eye-closure time ($t_c$) from the sensor;
exponentiating the eye-closure time ($t_c$);
moving averaging the exponentiation of the eye-closure time ($t_c$) and the eye-open time ($t_o$), respectively, in time-series manner;
calculating the degree of danger; and
comparing the calculated degree of danger with the predetermined threshold (Kt).

5. A method of doze-off driving determination, comprising:
receiving an eye-open time ($t_o$) and an eye-closure time ($t_c$) from a sensor;
exponentiating the eye-closure time ($t_c$);
moving averaging the exponentiation of the eye-closure time ($t_c$) and the eye-open time ($t_o$), respectively, in time-series manner;
calculating a degree of danger by dividing $T_c^n$ by $T_o$, wherein 'n' is an integer; and
comparing the calculated degree of danger with a predetermined threshold (Kt).

* * * * *